(12) United States Patent
Magerl et al.

(10) Patent No.: US 7,628,816 B2
(45) Date of Patent: Dec. 8, 2009

(54) SPONDYLODESIS DEVICE

(76) Inventors: Friedrich Magerl, Tutilostrasse 17h, 9011 St. Gallen (CH); Christian Widmer, Witterstrasse 24, 9430 St. Margrethen (CH); Roger Stadler, Munchhaldenstrasse 7, 8008 Zurich (CH)

( * ) Notice: Subject to any disclaimer, the term of this patent is extended or adjusted under 35 U.S.C. 154(b) by 50 days.

(21) Appl. No.: 10/554,062

(22) PCT Filed: Apr. 23, 2004

(86) PCT No.: PCT/CH2004/000244
§ 371 (c)(1),
(2), (4) Date: Jul. 30, 2006

(87) PCT Pub. No.: WO2004/093749
PCT Pub. Date: Nov. 4, 2004

(65) Prior Publication Data
US 2007/0213820 A1 Sep. 13, 2007

(30) Foreign Application Priority Data
Apr. 23, 2003 (EP) .................................. 03405284

(51) Int. Cl.
*A61F 2/44* (2006.01)

(52) U.S. Cl. .................. 623/17.16; 623/17.11; 606/246; 606/249; 606/280; 606/71

(58) Field of Classification Search .............. 623/17.11, 623/17.12, 17.13, 17.14, 17.15, 17.16; 606/61, 606/606, 246, 248, 280, 70, 71, 281, 282, 606/283, 284, 285, 286, 287, 288, 289, 290, 606/291, 292, 293, 294, 295, 296, 297, 298, 606/299

See application file for complete search history.

(56) References Cited

U.S. PATENT DOCUMENTS

| 5,000,166 | A | * | 3/1991 | Karpf ........................ 606/61 |
| 5,269,784 | A | * | 12/1993 | Mast ........................... 606/69 |
| 5,360,430 | A | | 11/1994 | Lin |
| 5,364,399 | A | * | 11/1994 | Lowery et al. .............. 606/295 |
| 5,443,515 | A | | 8/1995 | Cohen et al. |
| 5,487,743 | A | * | 1/1996 | Laurain et al. ............... 606/61 |
| 5,490,851 | A | * | 2/1996 | Nenov et al. ................. 606/61 |
| 5,607,425 | A | * | 3/1997 | Rogozinski .................. 606/61 |
| 5,707,372 | A | * | 1/1998 | Errico et al. ................. 606/61 |
| 5,755,796 | A | | 5/1998 | Ibo et al. |
| 5,836,948 | A | * | 11/1998 | Zucherman et al. .......... 606/61 |
| 5,865,846 | A | * | 2/1999 | Bryan et al. ................. 128/898 |

(Continued)

FOREIGN PATENT DOCUMENTS

| EP | 0179695 | 4/1986 |
| FR | 2727005 | 5/1996 |
| GB | 1243353 | 8/1971 |
| WO | WO 00/22998 | 4/2000 |
| WO | WO 00/24343 | 5/2000 |

*Primary Examiner*—Eduardo C Robert
*Assistant Examiner*—Jan Christopher Merene
(74) *Attorney, Agent, or Firm*—Browdy & Neimark, PLLC (57) ABSTRACT

Disclosed is a device comprising at least one intervertebral implant (3) and at least one plate (4,5) that is to be connected to the intervertebral implant (3) and an adjacent spine (21-23). The intervertebral implant (3) is connected to at least two spaced-apart plates (4,5). One end of both plates (4,5) respectively forms a fixable joint along with the intervertebral implant (3). Preferably, at least one of the plates (5,4) is embodied in a Z-shaped or L-shaped manner. The inventive device provides for great adaptability to the anatomic characteristics of the spinal column and a modular structure while the number of parts is kept small.

14 Claims, 5 Drawing Sheets

U.S. PATENT DOCUMENTS

| | | |
|---|---|---|
| 5,951,555 A * | 9/1999 | Rehak et al. .................. 606/61 |
| 6,074,423 A * | 6/2000 | Lawson .................. 623/17.11 |
| 6,156,037 A | 12/2000 | LeHuec et al. |
| 6,190,413 B1 * | 2/2001 | Sutcliffe .................. 623/17.11 |
| 6,306,138 B1 | 10/2001 | Clark et al. |
| 6,336,927 B2 * | 1/2002 | Rogozinski .................. 606/61 |
| 6,613,051 B1 * | 9/2003 | Luk et al. .................. 606/61 |
| 7,090,676 B2 * | 8/2006 | Huebner et al. ............... 606/71 |
| 7,214,226 B2 * | 5/2007 | Alleyne ....................... 606/61 |
| 2001/0007072 A1 | 7/2001 | Steiner et al. |
| 2005/0071006 A1 * | 3/2005 | Kirschman ............... 623/17.11 |
| 2009/0054987 A1 * | 2/2009 | Chin et al. ............... 623/17.16 |

* cited by examiner

SPONDYLODESIS DEVICE

The invention relates to a device for spondylodesis and in particular to a device for anterior intersomatic spondylodesis of the cervical spine, with at least one intervertebral implant, and with at least one connecting plate which is to be connected to the intervertebral implant and to an adjacent vertebra.

Spondylodesis is understood as surgical stiffening or blocking of a portion of the spinal column. For this purpose, in the traditional method, use is made of bone or of a bone replacement material which is inserted between the vertebral bodies, so-called intersomatic spondylodesis, or applied across the rear elements of the vertebrae, so-called dorsal spondylodesis. Over the course of time, this results in the creation of an osseous bridge which connects the vertebrae in such a way that they are no longer able to move relative to one another. To allow ossification to take place, it is necessary for the relevant portion of the spinal column to be immobilized. This is achieved by means of suitable implants. These can be connected to the intervertebral implant or can be fitted independently of the latter.

Indications for spondylodesis include pain, spinal cord compression, nerve root compression and defective posture which are not able to be influenced by conservative therapeutic measures. Pain may in principle radiate from all pathologically altered structures of the spinal column. Narrowing of the spinal canal or of the intervertebral foramina is mainly responsible for the development of spinal cord compression or nerve root compression. By performing a surgical procedure, the pathological defects are eliminated and the stability of the spinal column is restored by the spondylodesis.

Since intersomatic spondylodesis always involves the reaming out of intervertebral disks, and this impairs the stability of the spinal column, this stability always has to be restored. This can be done, for example, using pressure-resistant bone chips which are taken from the patient, so-called autogenous bone chips, and are inserted between the vertebral bodies. Since the load-bearing capacity of such chips is often uncertain, and since their availability is limited, and since in addition the morbidity caused by collecting samples of bone chips may be considerable, the use of autogenous bone chips is increasingly being replaced by the use of intervertebral implants, also called cages, made from exogenous materials.

An intervertebral implant functions as a pressure-absorbing spacer which stabilizes the spondylodesis, secures the adjustability of the vertebral bodies relative to one another and ensures that a solid osseous bridge forms between the adjacent vertebral bodies. Bones or bone replacement material filled into the intervertebral implants and/or applied around them form a matrix for the new bone formation. The stability of the spondylodesis is crucial for the ossification process. Movements occurring within the spondylodesis delay or prevent its osseous consolidation.

Many intervertebral implants connected to vertebrae by a plate have been disclosed in the prior art.

For example, U.S. Pat. No. 6,235,059 B discloses a device with an intervertebral implant with which two vertebrae can be stabilized on one another. A plate with two arms is secured on the intervertebral implant and is connected in a rigid or pivotable manner to said intervertebral implant. Each arm has a continuous hole through which a bone screw can be screwed into the corresponding vertebral body. Adaptation to the particular anatomical circumstances, and in particular to the sagittal curvature, is very limited in this case. The intervertebral implant can only be connected to the adjacent vertebrae.

WO 00/24343 discloses a device with an intervertebral implant which has windings about the circumference and can be screwed in the manner of a screw in between the vertebrae. A wing-shaped plate with two arms is secured on a front end of the intervertebral implant. It is secured here in such a way that the plate can be moved in order to adapt to the anatomical circumstances. The two arms of the plate each have an oblong hole for receiving a bone screw. In this device too, the intervertebral implant can be connected only to the adjacent vertebrae. The adaptability to the anatomical circumstances is very limited.

FR 2 727 005 discloses a device with several intervertebral implants which are connected to one another by a common band. The band has holes for securing the band and in each case an intervertebral implant and holes for receiving a bone screw. It is true that several intervertebral implants can be connected to one another with this device, but the adaptability to the anatomical circumstances is also very limited here. To ensure such adaptability, different bands would have to be made available in this case. The distances between the intervertebral implants is predetermined.

EP 0 179 695 A discloses an intervertebral implant on which eyelets are formed, with which eyelets the implant can be screwed securely onto adjacent vertebrae. Here once again, the adaptability to anatomical circumstances is very limited. In particular, it is generally not possible in this case to fit the bone screws into the vertebral body at the desired location. Moreover, only two vertebrae can be connected with one intervertebral implant.

U.S. Pat. No. 5,360,430 discloses an intervertebral implant which completely or partially replaces a vertebra, is secured by plates to the upper and lower vertebrae, and permits a certain unsprung or sprung mobility between these vertebrae.

U.S. Pat. No. 5,443,515 likewise discloses an implant intended to replace a vertebral body. It is made of tantalum foam.

Because of the considerable anatomical variations existing between individuals and also caused by disease, in particular the anatomical variations in the cervical spine, stabilization of intervertebral implants with conventional plates necessitates a large range of plates of different lengths and with different distances between their holes. The length of the plates is dependent on the position of the upper and lower end holes. If, in the case of multi-level spondylodesis, the plates are secured only on the end vertebrae, there is a danger that the plates will tear off at one end vertebra. It is therefore advisable also to fix the plates by screws to the vertebral bodies lying between the end vertebrae. However, the screw holes provided for this purpose in conventional plates do not always lie exactly in a way that allows the screws in question to be fitted correctly into the vertebral bodies lying between the end vertebrae. In addition, when using different plate types, only one screw can be secured in each case in the vertebral body.

The object of the invention is to make available a device of this type which can be optimally adapted to the particular anatomical circumstances.

In a device of the generic type, the object is achieved by the fact that the intervertebral implant is connected to two plates which are arranged at a distance from one another, one end of each of the two plates forming a fixable joint together with the intervertebral implant. The two plates connected to the intervertebral implant can be moved independently of one another in several degrees of freedom and can be fixed at a stable angle in a desired end position. An important advantage of the device according to the invention is that it is also possible to perform multi-level spondylodesis, with adjacent intervertebral implants being able to be connected directly to one another. This affords an especially high degree of stability and thus of reliability. The intervertebral implants and the plates thus form a particularly stable unit. Different sizes of intervertebral implants can also be combined and can be connected to one another at stable angles by different plates. In particular, adaptation to different curvatures of the spinal column and to different distances between intervertebral implants and vertebrae is also possible. The invention is particularly suitable for plates which are not plastically deformable and are made, for example, of titanium or a composite material.

The device is especially suitable for spondylodesis of the cervical spine. It is recommended in this case to secure the spondylodesis with plates fixed to the anterior face of the cervical vertebral bodies. A modular system in particular is possible, which is advantageous both in terms of production and also in practice. The adaptability can be achieved with a surprisingly small range of individual parts.

According to a development of the invention, at least one plate is Z-shaped or L-shaped. A particularly high degree of adaptability and a particularly stable connection is possible with such plates. Z-shaped plates are suitable in particular for connecting adjacent intervertebral implants and, consequently, for stabilizing three vertebrae. Such Z-shaped plates can be anchored in a central area for example with two bone screws. L-shaped plates likewise permit securing of such plates with two bone screws. In the same way, more than three vertebrae or more than two intervertebral implants can be connected to one another. Also suitable as implant bridges are rectilinear plates which are secured by fixable joints to the intervertebral implants and by bone screws to the vertebral bodies lying between intervertebral implants. A configuration is also conceivable in which two intervertebral implants are fixed to one another not directly by a connecting plate (implant bridge), but indirectly via the vertebral bodies lying between the two intervertebral implants. For this purpose, short plates are provided which are secured by fixable joints to the respective intervertebral implant and by bone screws to the vertebral body, in which case the plate arranged on the upper intervertebral implant is directed downward and the plate arranged on the lower intervertebral implant is directed upward such that the plate ends with the bone screws lie alongside one another on the middle vertebra. In this way, each of the two intervertebral implants is then connected to the middle vertebra by a plate and at least one bone screw.

The invention also relates to a kit for producing a device as claimed in claim 1.

Illustrative embodiments of the invention are explained in more detail below with reference to the drawings, in which.

Figure 10:
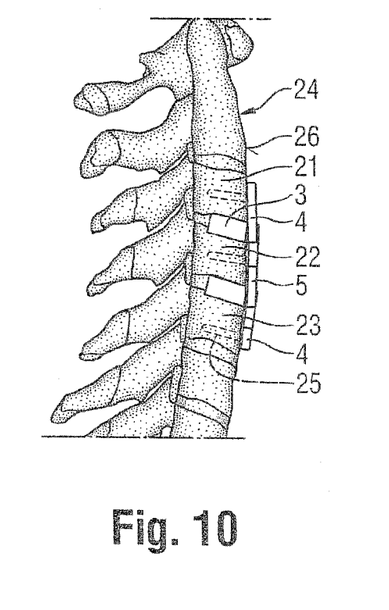
FIGS. 10-15 show diagrammatic views of a portion of a spinal column, each with a device according to the invention connecting vertebrae to one another.
Figure 11:
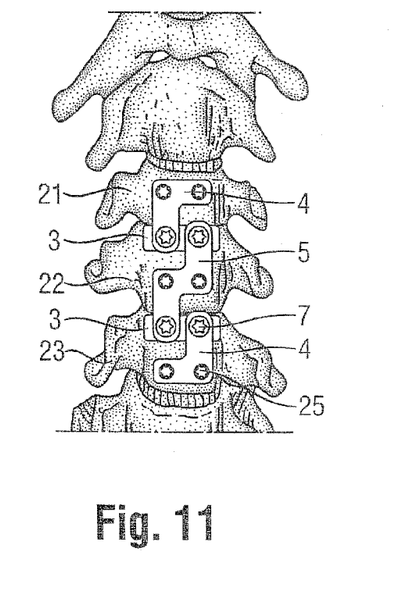

The device 1 shown in FIGS. 1 to 4 comprises two intervertebral implants 3 which, according to FIGS. 10 and 11, are each inserted into the intervertebral disk space between adjacent vertebrae 21, 22 and 22, 23, respectively, of a spinal column 24. The vertebrae 21 to 23 are here in particular vertebrae of the cervical spine, reference number 26 designating the anterior face of the cervical spine. The esophagus and major blood vessels (not shown here) lie to the left in FIG. 10 in front of the anterior face.

The two intervertebral implants 3 are made of metal, in particular titanium, or of a suitable plastic and constitute intersomatic and pressure-absorbing bodies. They each have a recess 20 which opens to the outside and serves to receive bone or a bone replacement material. The patient's bone grows through the recesses 20 so that an osseous bridge forms between the adjacent vertebrae 21, 22 and 22, 23, respectively. The vertebrae 21, 22 and 23 can thus be firmly connected to one another.

The two intervertebral implants 3 are firmly connected to one another by a Z-shaped plate 5. According to FIG. 2, this plate 5 has two arms 5a and 5b and also a central area 5c extending transversely with respect to these. The two arms 5a and 5b are preferably of identical design, so that the plate 5 is rotationally symmetrical in relation to a center point P. At a free end of each of the two arms 5a there is a hemispherical depression 27 with a centrally extending through-opening 17. These hemispherical depressions 27 and the through-openings 17 in each case receive a ball-head screw 7 which is screwed via a threaded shank 12 into a bore 13 of an intervertebral implant 3. The ball-head screws 7 each have a head 9 with a tool socket 8 and a likewise hemispherical underside 10. Arranged between the shank 12 and the head 9 there is a neck 11 whose diameter is smaller than that of the shank 12 and of the through-opening 28. The hemispherical underside 10 bears on the hemispherical depression 27. When the two screws 12 are firmly screwed into the respective intervertebral implant 3, the plate 5 is fixed at its two free ends securely on the respective intervertebral implant 3 by clamping. The clamping faces are formed by a hemispherical surface 15 and a likewise hemispherical surface 14 of the corresponding intervertebral implant 3. If the two ball-head screws 7 are not screwed in fully, the two connections of the plate 5 to the intervertebral implant 3 each form a kind of ball joint, in each case permitting movements in several degrees of freedom at both attachment points.

The plate 5 and the two intervertebral implants 3 can thus be moved relative to one another and, in each desired position, these parts can be connected to one another at a stable angle by tightening of the screws 7. After the ball-head screws 7 have been tightened, the two intervertebral implants 3 and the Z-shaped plate 5 form a stable unit. If necessary, the screws 7 can be loosened at any time and, in this way, the movable state can be restored.

Figure 1:
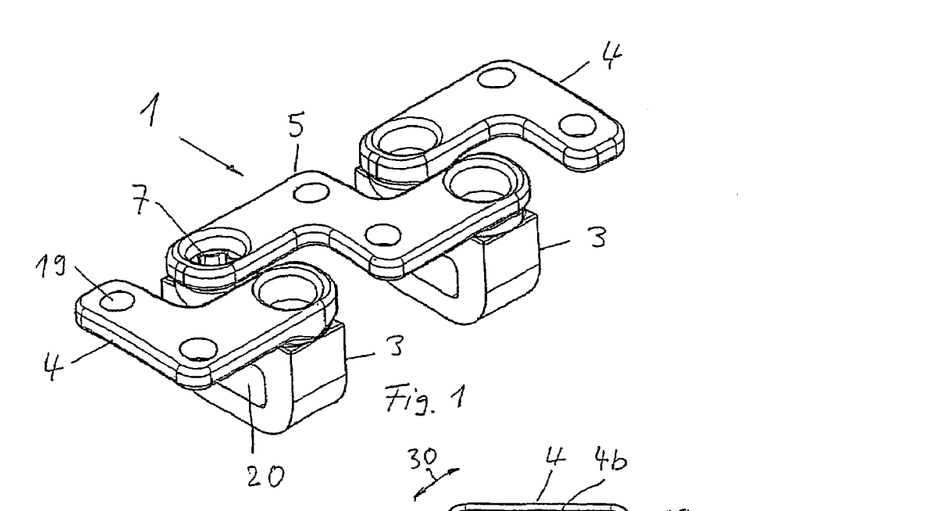
FIG. 1 shows a diagrammatic perspective view of a device according to the invention.
Figure 2:
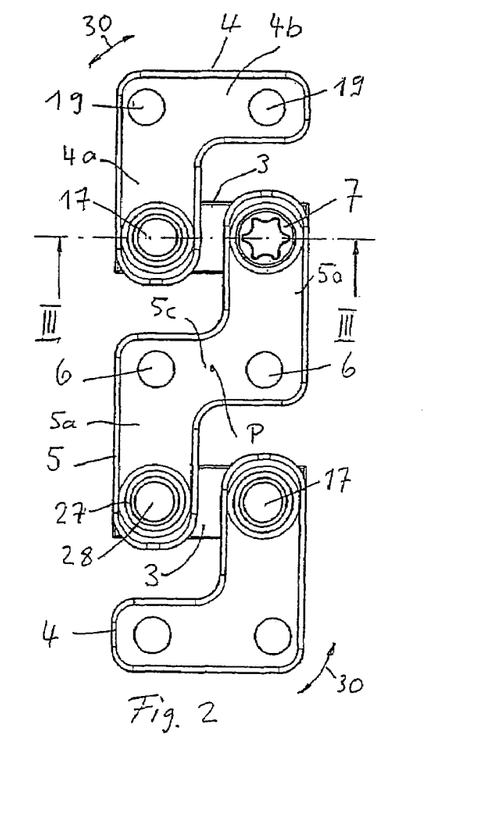
FIG. 2 shows a further view of the device according to the invention from FIG. 1.
Figure 3:
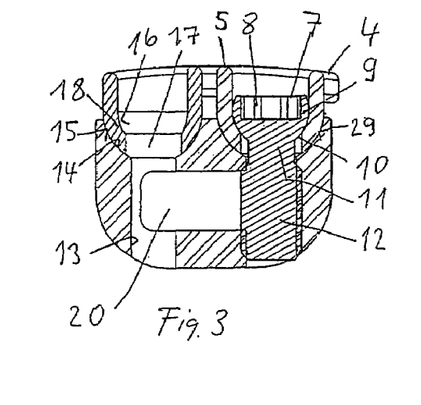
FIG. 3 shows a cross section along line III-III in FIG. 2.

Arranged on each of the two intervertebral implants 3 there is in each case a further plate 4 which is preferably L-shaped or corner-shaped. These plates 4 each have two arms 4a and 4b, which may be identical or different. The arm 4a has, on its underside, a spherical joint part 18 with a spherical inner face 16 and a likewise hemispherical outer face 15. The joint part 18 has a through-opening 17. The joint part 18 sits in a hemispherical depression 14 of the corresponding intervertebral implant 3. To secure the plate 4 on the corresponding intervertebral implant 3, a ball-head screw 7 is fitted from above into the joint part 18, in the same way as for securing the Z-shaped plate 5, and is screwed into the bore 13 of the corresponding intervertebral implant 3. In FIGS. 1-3, these screws 7 have been omitted for the sake of clarity. Before the screw 7 is tightened, the corresponding plate 4 can be moved, by virtue of the ball-joint connection, and adapted to the anatomical circumstances. When the optimal position is reached, the corresponding screws 7 are tightened and the plates 4 are in this way fixed at a stable angle in relation to the corresponding intervertebral implant 3.

Figure 7:
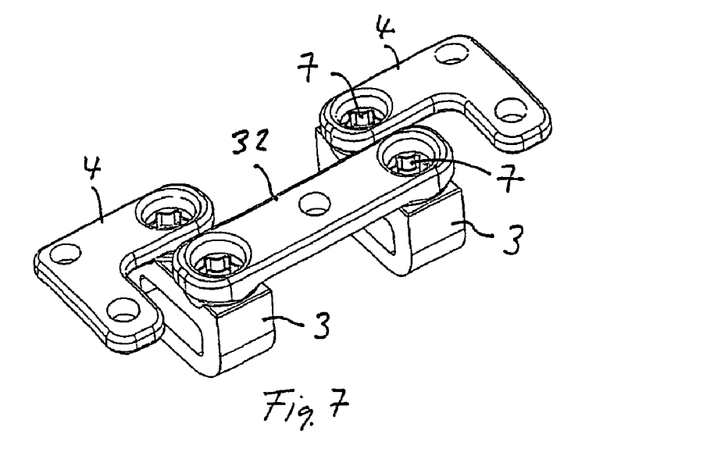
FIG. 7 shows a perspective view of a variant of the device according to the invention.

In the arm 4*b*, the two plates 4 each have two through-openings 19 which are arranged at a distance from one another and which each serve to receive a bone screw 25, as is shown diagrammatically in FIG. 7. Such bone screws 25 are known per se. The connection can be made with a stable angle by using a screw in accordance with WO 01/30251 or alternatively can also be made movable. With these screws 25, the two plates 4 are secured in the corresponding vertebral body 21, 23. These bone screws 25 should lie as far as possible at the center of the corresponding vertebral body 21, 23. Otherwise, their fit could be adversely affected. Moreover, these screws should not penetrate into a healthy intervertebral disk, and, in addition, the arms 4*b* should not touch a healthy intervertebral disk. This would lead to destruction or degeneration of the intervertebral disks concerned. By virtue of the adjustability of the plates 4, it is now possible to orient them in such a way that the screws, as has been explained above, can be screwed at suitable positions into the vertebral bodies 21, 23. Likewise, it is in this way possible to ensure that the arms 4*b* do not touch an intervertebral disk.

Said adjustability of the plates 4 allows them to be adapted to the different curves and shapes of the anterior face 26 of the cervical spine. This is even possible when intervertebral implants 3 as desired do not protrude from the anterior face 26. The intervertebral implants 3 ought not to protrude from the anterior face 26 because they could then cause damage to the structures situated in front of the cervical spine 24, in particular the esophagus and major blood vessels.

With the ball-head screws 7 tightened, the two plates 4 thus each connect an intervertebral implant 3 to a vertebral body 21, 22 and 22, 23 at a stable angle. The plate 5 connects the two intervertebral implants 3 to one another at a stable angle. In the central and transversely extending area 5*c*, the plate 5 also has two through-openings 6 which each receive a bone screw 25, these bone screws 25 being screwed into the central vertebral body 22 and thus anchoring the plate 5 on this central vertebral body 22. Here too, an angularly stable or movable connection is possible between plate 4 and bone screw 25.

Figure 4:
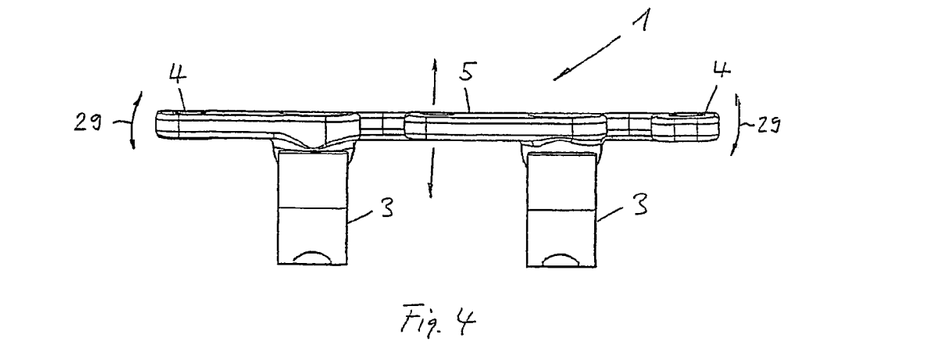
FIG. 4 shows a further view of the device according to the invention from FIG. 1.
Figure 5:
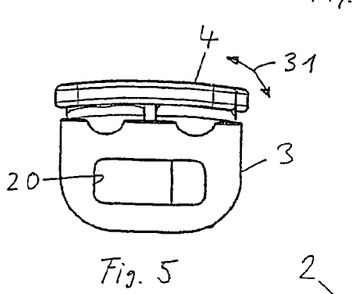
FIG. 5 shows a further view of the device according to the invention from FIG. 1.

According to FIGS. 4 and 5, the two plates 4 and the plate 5 can lie in one plane. Because of said joint connections, however, a plane arrangement of this kind is not essential. For example, the two plates 4 can be pivoted upward or downward, according to the double arrows 29 in FIG. 4, independently of one another and in a comparatively wide range. These two plates 4 can also be pivoted independently of one another according to double arrows 29 to 31 in FIGS. 2, 4, 5 and 6.

By virtue of the ball-joint connections, however, other movements and degrees of freedom are also possible here. Thus, in particular the pivot movement indicated by the double arrow 31 in FIG. 5 is available. Each possible position can be fixed by tightening of the corresponding ball-head screw 7. In this way, as has been explained above, optimal adaptation to the particular anatomical circumstances is possible.

Figure 6:
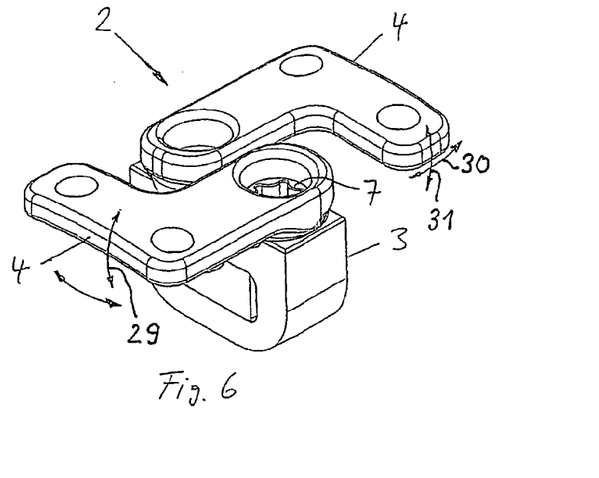
FIG. 6 shows a perspective view of a variant of the device according to the invention.

FIG. 6 shows a device 2 according to the invention, which only has one intervertebral implant 3 and two L-shaped or corner-shaped plates 4. As has already been explained above, the plates 4 are each secured with a ball-head screw 7 on the intervertebral implant 3. As has been explained above, the connection is in the manner of a ball joint. As has been explained above, the two plates 4 can likewise be moved before the two screws 7 are tightened. Only one of the two ball-head screws 7 is shown in FIG. 6. In the embodiment shown, the two plates 4 are of identical design. However, the plates 4 can also be different, for example of different lengths. They do not necessarily have to be L-shaped or corner-shaped, and instead can also be rectilinear elongate plates. This applies also to the plates 4 of the device 1. The device 2 is used to connect two adjacent vertebrae 21, 22 and 22, 23. Of course, several such devices 2 can be fitted on a spinal column 24. However, the corresponding intervertebral implants 3 are then only interconnected across intermediate vertebrae. A direct connection, as in the device 1, is thus not present here.

The plates 4 and 5 and the intervertebral implants 3 are preferably made of a suitable plastic, for example of a fiber-reinforced plastic. Such plastics are known per se and have the important advantage that they are transparent to X-rays. With such materials, it is also possible to produce very stable plates 4 and 5 which also have a high degree of flexural rigidity. It is thus possible to minimize movements within the spondylodesis and, consequently, the risk of a sometimes serious secondary dislocation of the implant. In principle, however, the plates 4 and 5 can also be made of another material, for example of titanium.

A device is also possible (not shown here) with more than two intervertebral implants 3 which are connected directly to one another by a corresponding number of Z-shaped plates 5. For example, such a device can comprise three intervertebral implants 3 connected to one another by two Z-shaped plates 5. An L-shaped plate 4 is then also secured on each of the two outer intervertebral implants.

Figure 9:
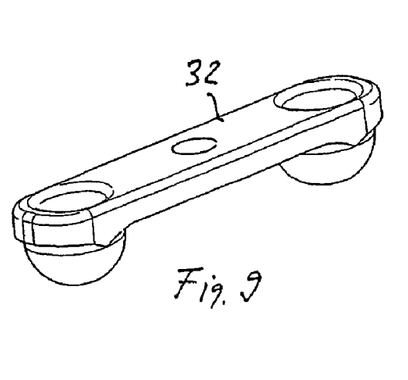
FIG. 9 shows a perspective view of a rectilinear plate with two joints.

FIG. 7 shows an embodiment of a device according to the invention which has two L-shaped plates 4 and a rectilinear plate 32. At each of its ends, the long plate 32 is connected to an intervertebral implant 3 via a ball-head screw 7. The connections to the intervertebral implants 3 are joints which have a polyaxial mobility and can be fixed by tightening of the screws 7. The configuration of the long and rectilinear plate 32 can be seen in FIG. 9.

Figure 8:
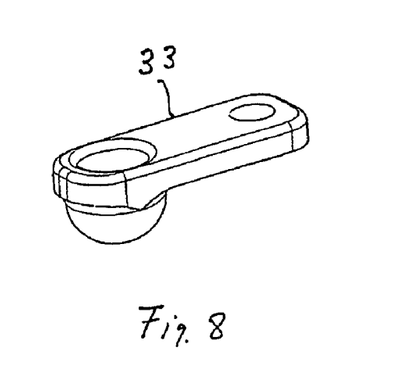
FIG. 8 shows a perspective view of a rectilinear plate with a joint.
Figure 13:
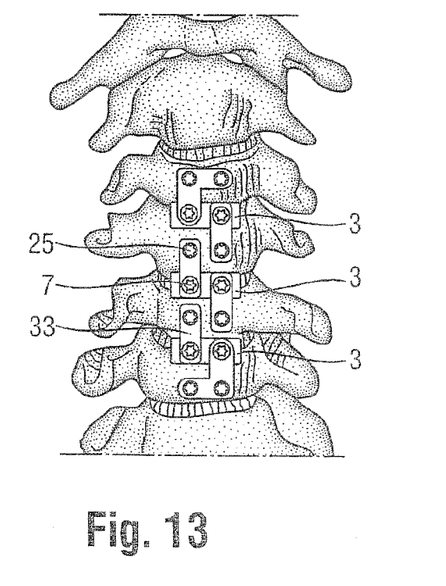

FIG. 8 also shows a comparatively short plate 33 which can receive a ball-head screw 7 and a bone screw 25 and which can be used in particular according to FIG. 13.

A method for stiffening a portion of a spinal column with the device according to the invention is explained in detail below.

After suitable exposure of the portion of the spinal column that is to be stiffened, the affected intervertebral disk is reamed out. By means of a suitable instrument, the reamed intervertebral disk space is widened and enlarged. A suitable intervertebral implant 3 is now chosen and is inserted into the reamed intervertebral disk space, where it is wedged between the adjacent vertebrae. If appropriate, a further intervertebral disk is reamed out and a further intervertebral implant 3 is inserted.

Distances between the intervertebral implant 3 or intervertebral implants 3 and suitable positions for the bone screws are now determined. In the case of two intervertebral implants 3, the distance between these is also measured. Suitable plates 4 and if appropriate 5 are selected according to these distances are fitted loosely on the intervertebral implant 3 or on the intervertebral implants. The plates 4 are chosen such that they do not touch adjacent intervertebral disks, as can be seen in FIGS. 7 and 8. The loosely fitted plates 4 and 5 are now placed on the vertebrae and fixed with bone screws 25. The plates 4 and if appropriate 5 are now connected firmly to the intervertebral implant 3 or intervertebral implants by tightening of the screws 7.

FIGS. 10 and 11 show three vertebrae 21 to 23 which are connected to one another by a device according to the invention. As can be seen, the plate 5 connects two intervertebral implants 3 to one another and is additionally connected to the vertebra 22 by bone screws 25. If only two vertebrae are connected to one another, the device 2 according to FIG. 6 is used, in which a Z-shaped plate 5 is not provided.

FIGS. 11-15 show five of the possible embodiments of the device according to the invention with which two or more vertebrae can be connected to one another. In FIGS. 11 to 15, the cervical spine is seen from the front and in FIG. 10 it is seen from the side.

Figure 14:
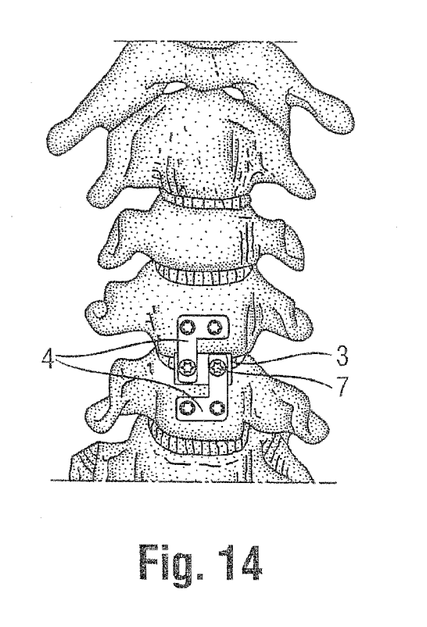

FIG. 14 shows a connection of two vertebrae with the aid of two L-shaped plates 4 and one intervertebral implant 3. The L-shaped plates 4 are each secured to the vertebral bodies by two bone screws 25 and to the intervertebral implant 3 by in each case one ball-head screw 7.

FIG. 11 shows a connection of three vertebrae 21-23. The intervertebral implants 3 are connected directly to one another by an implant bridge. The latter consists in this case of a Z-shaped plate 5. The Z-shaped plate 5 is secured to the body of the central vertebra 22 by two bone screws 25.

FIG. 10 shows a view of a cervical spine from the -side, with the device according to the invention from FIG. 11 bearing on the anterior of the cervical vertebral bodies.

Figure 12:
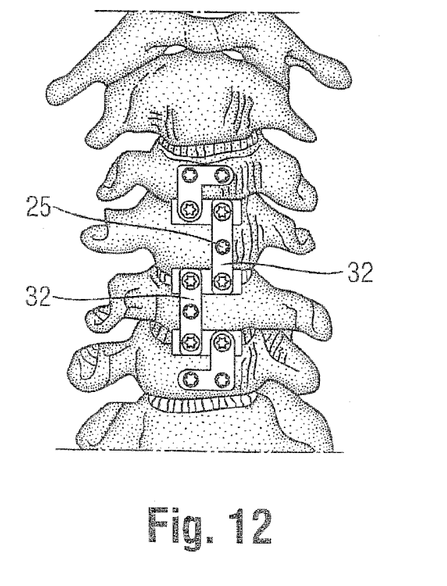

FIG. 12 shows a connection of four vertebral bodies, rectilinear plates 32 forming the implant bridge to the intervertebral implants 3. Each rectilinear plate 32 is secured by a bone screw 25 to the vertebral bodies lying below the plate 32 in question.

In the illustrative embodiment according to FIG. 13, three intervertebral implants 3 are connected to one another not directly by implant bridges, but indirectly via the vertebral bodies lying between two respective intervertebral implants 3, by means of short plates 33 being secured on the intervertebral implants 3 and on the vertebral bodies lying between these.

Figure 15:
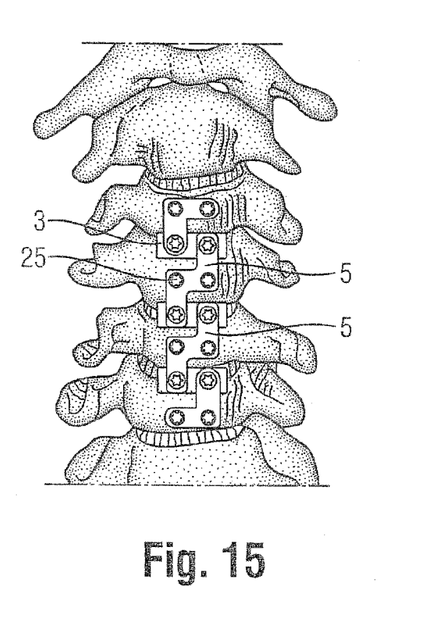

FIG. 15 shows a connection of four vertebrae, with Z-shaped plates 5 again forming the implant bridges to intervertebral implants 3. The Z-shaped plates 5 are each secured by two bone screws 25 to the vertebral body located below the respective plate. The connection to the upper vertebra and lower vertebra is effected in the manner described for FIG. 14. The connection is in this case produced exclusively with Z-shaped plates 5.

An important advantage of the invention is that the implant according to the invention, by virtue of the articulated cage-plate connections, a range of plates of different lengths and intervertebral implants of different sizes (heights) can be precisely adapted to the individual and sometimes very different anatomical circumstances, in particular the anterior face of the cervical spine. The latter may be plane, more or less convex or even concave or can be alternately convex or concave from vertebra to vertebra. The cervical spine, seen from the front, may also be slightly crooked or twisted slightly about the longitudinal axis. All of this can be compensated by the free mobility of the plates.

The present invention is concerned not only with stable connections between the implants and with stable connections between the end vertebrae of the spinal column portion stiffened with the aid of the device, but above all with the complete adaptability of the device to the respective anatomical circumstances (curvatures, dimension ratios, irregularities). This adaptability is especially important on the cervical spine, because the implants must not protrude from the anterior face of the cervical spine. They must not be thicker than 2 mm to at most 3 mm and they have to bear well on the vertebral bodies. Otherwise, there is a danger of a serious complication arising, for example if structures lying near the anterior face of the cervical spine, such as the esophagus and blood vessels, become eroded over the course of time.

Our device is distinguished by its low profile, i.e. by a low overall height.

The adaptability of the device according to the invention is due in particular to
- the lockable ball joints, each with three degrees of freedom
- a range of plates of different lengths (both L-shaped plates and Z-shaped plates)
- a range of intervertebral implants of different sizes.

LIST OF REFERENCE LABELS

1 device
2 device
3 intervertebral implant
4 plate
4a arm
4b arm
5 plate
5a arms
5b arms
5c central area
6 through-opening
7 ball-head screw
8 tool socket
9 head
10 underside
11 neck
12 threaded shank
13 bore
14 surface
15 surface
17 through-opening
18 joint part
19 through-opening
21-23 vertebrae
24 cervical spine
25 bone screw
26 anterior face
27 depression
28 through-opening
29-31 double arrows
32 rectilinear plates
33 short plates
P center point

The invention claimed is:

1. A device for spondylodesis for anterior intersomatic spondylodesis of the cervical spine, comprising: an intervertebral implant with at least two hemispherical depressions, where the intervertebral implant functions as a pressure-absorbing spacer which is adapted to stabilize the spondylodesis and ensures that a solid osseous bridge forms between adjacent vertebral bodies, wherein the intervertebral implant is formed as a unit having only a single recess therein that extends through the implant to open on opposite sides of the implant to an outside of the implant and adapted to face along the longitudinal axis of the spinal column when implanted;

wherein the intervertebral implant is connected to at least two plates;

wherein the intervertebral implant extends transversely to the at least two plates which are arranged at a distance from one another, one end of each of the plates form a fixable joint together with the intervertebral implant;

wherein a second intervertebral implant is provided;

wherein one of the plates is L-shaped or I-shaped and adapted to connect with an adjacent vertebra and the other plate is Z-shaped and connects with said second intevertebral implant;

wherein a third plate is connected to said second intervertebral implant, wherein said third plate is L-shaped or I-shaped, wherein each of the plates have, at least at one end, a hemispherical joint part formed as a unit, which protrudes transversely down from each plate;

wherein said joint part of each plate has a passage for a locking screw and engages in one of the hemispherical depressions of their respective intervertebral implant to form a ball joint.

2. The device as claimed in claim 1, characterized in that at least one plate, in a central area extending transversely with respect to the longitudinal axis of the spinal column, has at least one passage for a bone screw, so that this plate can be adapted to connect to a vertebra.

3. The device as claimed in claim 2, wherein said area has two said passages arranged at a distance from one another and each intended for a bone screw.

4. The device as claimed in claim 1, wherein at least two plates are each connected to an intervertebral implant via a ball joint that is polyaxial.

5. The device as claimed in claim 1, wherein the two plates each have, in an arm extending transversely with respect to the longitudinal direction of the spinal column, at least two passages which are arranged at a distance from one another and each receive a bone screw.

6. The device as claimed in claim 1, wherein at least one plate and/or an intervertebral implant is/are made of a material transparent to X-rays.

7. The device as claimed in claim 1, characterized in that the device is provided for spondylodesis of the cervical spine.

8. The device as claimed in claim 1, wherein an upper side of the at least one intervertebral implant on which the at least two plates are engaged is at least partially flat.

9. The device as claimed in claim 8, wherein the opposite sides of the implant is capable to respectively engage adjacent vertebral bodies and are at least partially flat.

10. A kit for producing the device as claimed in claim 9, having two intervertebral implants; wherein a first of said two plates for connecting the intervertebral implants to adjacent vertebras is L-shaped and a second of two plates is Z-shaped, and wherein the two intervertebral implants each have two bores which are arranged at a distance from one another and each receive a locking screw;

wherein opposite ends of the Z-shaped plate each have said hemispherical joint part respectively engaged in the hemispherical depression on each of the two invertebral implants forming said ball joints.

11. The kit as claimed in claim 10, wherein the intervertebral implants and the two plates each have at least one joint part for forming a ball joint.

12. The kit as claimed in claim 10, wherein the intervertebral implants and the two plates are made of a material transparent to X-rays.

13. The kit as claimed in claim 10, including a plurality of bone screws and a plurality of locking screws.

14. The kit as claimed in claim 13, wherein the locking screws are ball-head screws having a screw head which is substantially hemispherical on its underside.

* * * * *